US009636230B2

(12) United States Patent
Talwar

(10) Patent No.: US 9,636,230 B2
(45) Date of Patent: May 2, 2017

(54) INTERBODY FUSION IMPLANT AND SCREW GUIDE

(76) Inventor: Vikram Talwar, San Ramon, CA (US)

( * ) Notice: Subject to any disclaimer, the term of this patent is extended or adjusted under 35 U.S.C. 154(b) by 686 days.

(21) Appl. No.: 13/592,178

(22) Filed: Aug. 22, 2012

(65) Prior Publication Data
US 2013/0053964 A1    Feb. 28, 2013

Related U.S. Application Data

(60) Provisional application No. 61/575,639, filed on Aug. 25, 2011.

(51) Int. Cl.
| | | |
|---|---|---|
| A61F 2/44 | (2006.01) | |
| A61F 2/46 | (2006.01) | |
| A61B 17/16 | (2006.01) | |
| A61B 17/17 | (2006.01) | |
| A61B 17/70 | (2006.01) | |
| A61F 2/30 | (2006.01) | |
| A61B 17/86 | (2006.01) | |

(52) U.S. Cl.
CPC .......... *A61F 2/442* (2013.01); *A61B 17/1671* (2013.01); *A61B 17/1757* (2013.01); *A61B 17/7055* (2013.01); *A61F 2/4455* (2013.01); *A61F 2/4611* (2013.01); *A61B 17/863* (2013.01); *A61F 2002/3056* (2013.01); *A61F 2002/30672* (2013.01); *A61F 2002/30774* (2013.01); *A61F 2002/30785* (2013.01); *A61F 2002/30787* (2013.01); *A61F 2002/4687* (2013.01)

(58) Field of Classification Search
USPC .......... 623/17.11, 17.16; 606/80, 96–98, 99, 606/104
See application file for complete search history.

(56) References Cited

U.S. PATENT DOCUMENTS

| | | | | |
|---|---|---|---|---|
| 4,616,638 | A * | 10/1986 | Griggs | 606/104 |
| 4,858,601 | A * | 8/1989 | Glisson | 606/916 |
| 5,259,398 | A * | 11/1993 | Vrespa | 128/898 |
| 6,056,749 | A * | 5/2000 | Kuslich | 606/86 A |
| 6,077,267 | A * | 6/2000 | Huene | 606/916 |
| 6,319,254 | B1 * | 11/2001 | Giet et al. | 606/916 |
| 7,491,237 | B2 * | 2/2009 | Randall et al. | 623/17.11 |
| 7,658,879 | B2 * | 2/2010 | Solar | 264/278 |
| 7,892,239 | B2 * | 2/2011 | Warnick et al. | 606/99 |

(Continued)

*Primary Examiner* — Matthew Lawson
*Assistant Examiner* — Amy Sipp
(74) *Attorney, Agent, or Firm* — Heisler & Associate

(57) ABSTRACT

An interbody fusion implant fits between adjacent vertebrae for fixation during fusion thereof. Upper bores extend into a cephalid surface of the implant and preferably include threads therein. A guide tool is removably attachable to the implant which supports guide bores along centerlines aligned with the upper bores in the implant. A drill can pass along these guide bores to form holes in a vertebra adjacent the cephalid surface of the implant which is precisely aligned with the upper bores. A hybrid screw then passes through these holes in the vertebra adjacent the cephalid surface and threads into the upper bores to secure the implant to the adjacent cephalid vertebra. Bone screws can also be used to secure the implant to caudal vertebra by passing through bores passing through the implant, such that the implant is securely mechanically fastened to both cephalid and caudal vertebrae adjacent the implant.

10 Claims, 3 Drawing Sheets

(56) References Cited

U.S. PATENT DOCUMENTS

| | | | |
|---|---|---|---|
| 7,959,675 B2* | 6/2011 | Gately | 623/17.11 |
| 8,187,281 B2* | 5/2012 | Cresina et al. | 606/96 |
| 8,241,297 B2* | 8/2012 | Ashman | 606/96 |
| 8,277,510 B2* | 10/2012 | Kleiner | 623/17.16 |
| 8,518,044 B2* | 8/2013 | Sidebotham et al. | 606/80 |
| 2004/0126407 A1* | 7/2004 | Falahee | 424/423 |
| 2004/0153089 A1* | 8/2004 | Zdeblick et al. | 606/90 |
| 2004/0210227 A1* | 10/2004 | Trail et al. | 606/73 |
| 2005/0256578 A1* | 11/2005 | Blatt et al. | 623/17.15 |
| 2006/0106460 A1* | 5/2006 | Messerli et al. | 623/17.11 |
| 2006/0195109 A1* | 8/2006 | McGahan et al. | 606/80 |
| 2007/0123985 A1* | 5/2007 | Errico et al. | 623/17.11 |
| 2008/0103506 A1* | 5/2008 | Volpi et al. | 606/96 |
| 2008/0114370 A1* | 5/2008 | Schoenefeld | 606/96 |
| 2009/0012566 A1* | 1/2009 | Fauth | 606/247 |
| 2009/0030519 A1* | 1/2009 | Falahee | 623/17.16 |
| 2009/0118764 A1* | 5/2009 | Vaughan | 606/246 |
| 2009/0182341 A1* | 7/2009 | Link et al. | 606/99 |
| 2010/0145351 A1* | 6/2010 | Ashman | 606/96 |
| 2012/0271362 A1* | 10/2012 | Martineau et al. | 606/304 |
| 2012/0271424 A1* | 10/2012 | Crawford | 623/17.16 |
| 2013/0184827 A1* | 7/2013 | Lynn et al. | 623/17.16 |
| 2014/0031935 A1* | 1/2014 | Donner et al. | 623/17.11 |

* cited by examiner

INTERBODY FUSION IMPLANT AND SCREW GUIDE

CROSS-REFERENCE TO RELATED APPLICATIONS

This application claims benefit under Title 35, United States Code §119(e) of U.S. Provisional Application No. 61/575,639 filed on Aug. 25, 2011.

FIELD OF THE INVENTION

The following invention relates to implantable medical devices such as those used for interbody fusion between adjacent vertebrae, and especially between lumbar vertebrae and the sacrum. More particularly, this invention relates to interbody fusion implant cages which accommodate screws for attachment of the implant to vertebrae on both cephalid and caudal sides of the implant.

BACKGROUND OF THE INVENTION

Anterior lumbar interbody fusion (ALIF) has become an increasingly useful approach for fusing the lumbar spine. With ALIF procedures, a disk between adjacent vertebrae is removed and a fusion cage implant is inserted into the disk space. Through known techniques, bone growth through and around the cage is promoted to fuse the adjacent vertebrae together. In one ALIF procedure, a condition known as spondylolisthesis A can be treated (FIG. 1) by removal of the disk D between the sacrum (S1) and the adjacent lumbar vertebrae (L5). Other disk spaces between other adjacent disks can also be treated with this ALIF procedure.

There is some inherent difficulty in placing screws between the cage and a higher vertebra in the spine to fix the cage in place, particularly when fusing L5 and S1, and when the L5-S1 disk orientation is more angled toward the pubis rather than horizontally situated. Because of such angularity, upwardly angled bone screw supporting bores in the cage cannot be readily accessed. Accordingly, a need exists for a superior method for securing the interbody fusion cage implant to adjacent vertebrae which can be accessed conveniently in a wider variety of anatomical presentations for adjacent vertebrae to be fused.

SUMMARY OF THE INVENTION

With this invention, an improved spinal fusion cage implant and associated screw guide tool and screw orientation, as well as a unique hybrid screw are provided. Whereas the classic design of ALIF implants has been to go through the implant first and then into the end plate and vertebral body, with this type of cage and screw technique, the screw first enters the bone and then captures the implant cage distally in an upper cephalid surface of the cage. The angle of attack of this screw is more in-line with the approach to the anterior lumbar spine so that hybrid screws supporting and securing the cephalid vertebrae to the cage implant can be readily placed for fixation.

Utilizing this invention, the ALIF procedure begins as is known in the prior art. In particular, the disk is removed and the interbody cage implant is placed within the disk space. Bone screws are utilized to secure the cage to the sacrum (S1) or other lower caudal vertebrae adjacent the disk space. These bone screws extend diagonally, typically from an anterior side of the cage and then out of a caudal surface of the cage and into the end plate of the lower caudal vertebral body (typically S1). The cage has now been secured to the lower vertebral body (S1 or other lower vertebral body).

With this invention, a tool is provided having an elongate primary shaft or other element which can be removably attached to the anterior surface or other portion of the interbody fusion cage. In one embodiment, the cage implant has a threaded tool port bore extending into the anterior surface of the cage. The shaft of the tool has a threaded coupling tip which can thread into this tool port to removably secure the shaft to the cage implant. As rotational displacement of the primary shaft of the tool relative to the cage is important to control for this invention, the threaded tip of the primary shaft can abut some form of stop when precisely aligned where desired, rather than merely tightening through the threads alone, such that rotational alignment of the primary shaft relative to the cage is precisely controlled. Other forms of attachment could also be provided between the shaft and the cage implant which eliminates relative motion or misalignment between the shaft of the tool and the implant.

The tool includes a guide block or other structure extending up from the shaft or other implant engaging element of the guide tool. This guide block or other structure has at least one guide bore passing therethrough, and preferably a pair of guide holes which are oblique to each other to facilitate oblique screw alignment paths into an adjacent upper vertebral body (typically L5). The upper caudal surface of the interbody cage also includes at least one and typically two threaded bores extending thereinto at oblique angles. These bores are shown as blind bores. Optionally, these bores could extend through the cage and out a lower surface. In such an instance, a hole could be drilled in the lower vertebral body (e.g. S1), or a guide wire could pass through the bore and into the lower vertebral body so that a cannulated screw could extend through both the upper and lower vertebral body and through the implant. With use of two long screws at skewed angles to each other, secure rotation of the two intervertebral bodies and the cage would be maintained during bone fusion.

A centerline of these bores into the upper cephalid surface of the interbody implant are precisely aligned with the guide bores in the guide block of the tool. This precise alignment of the guide bores and the upper bores in the interbody cage allows a drill, and/or a bone screw to pass through the guide hole along an alignment axis which precisely aligns with the blind bore (or through bore) in the upper cephalid surface of the implant. Thus, a method for attachment of the hybrid screw of this invention or some other bone screw is facilitated between the upper vertebral body (typically L5) and the implant (and optionally also the lower vertebral body (typically S1)).

In a preferred form, this method includes first utilizing a drill which passes through the guide bore in the guide block or other guide tool structure and then drills the hole through the upper vertebral body (typically L5). This hole extends diagonally along the centerline from an anterior side of the higher vertebral body (typically L5) and through the lower end plate of this higher vertebral body, in alignment with the centerline of the upper bore in the cephalid surface of the implant.

The hybrid bore can then be precisely passed through the bore and engage the threaded blind bore in the upper surface of the cage implant to secure the upper vertebral body and the cage implant together (and optionally also the lower vertebral body as well). This hybrid bone screw can pass through the guide hole in the guide block, or the tool can be removed from the implant first (or rotated out of position) so that the guide block does not block the hybrid bone screw. The hybrid bone screw can then be passed through the hole in the upper vertebra and into the implant. The bore can be formed with a step so that a head of the hybrid screw can abut this step within the higher vertebral body. As an alternative, the head of the hybrid bone screw can merely abut the anterior side of the higher vertebral body, or the hybrid screw can be headless with just a torque applying tool interface at a proximal end thereof.

The hybrid screw preferably has finer threads at a tip thereof and cancellous threads for engaging bone closer to a proximal end of the screw. With such a configuration, the fine threads provide a secure attachment to the cage while the larger bone threads engage the upper vertebral body. Pitches of these threads can be identical or differential to provide a closing force between the cage and the upper vertebral body. A major diameter of the smaller threads is less than that of the bone threads so that the smaller threads can pass through the hole in the upper vertebral body without interference. In one embodiment, the hybrid screw only has the smaller threads at the tip and utilizes a head thereof, without bone threads or only a limited amount of bone threads, so that the head of the hybrid screw draws the higher vertebral body securely down against the cage when the hybrid screw is tightened. While two hybrid screws are shown for attachment of the implant to the upper vertebra, a number of screws could be as few as just one screw or more than two screws and still function according to this invention.

OBJECTS OF THE INVENTION

Accordingly, a primary object of the present invention is to provide an interbody fusion cage implant which can be secured to both cephalid and caudal vertebral structures adjacent the implant.

Another object of the present invention is to provide an interbody fusion cage which can be mechanically affixed in a space between the L5 vertebra and the S1 sacrum and be mechanically attached to both the L5 vertebra and the S1 sacrum to support the L5 vertebra and the S1 sacrum for interbody fusion thereof.

Another object of the present invention is to provide an implant and associated guide tool which facilitates precise formation of a hole in a vertebra or other structure on a cephalid side of the implant precisely located to align with a bore in the implant in advance of placement of a screw therein for fixation.

Another object of the present invention is to provide a method for forming holes in vertebra adjacent an interbody fusion cage implant and for placement of screws between an interbody fusion cage implant and adjacent vertebra for secure fixation during interbody fusion, especially of the L5/S1 joint.

Another object of the present invention is to provide a hybrid screw for fixation of an interbody fusion implant cage to an adjacent vertebrae or other structure, which screw has a distal portion adapted to thread into the implant cage and a proximal portion configured to both receive torque and to engage a vertebral structure to be held against the implant.

Other further objects of the present invention will become apparent from a careful reading of the included drawing figures, the claims and detailed description of the invention.

BRIEF DESCRIPTION OF THE DRAWINGS

FIG. 4 also shows in broken lines a variation on the hybrid screw where threads are only provided at a distal end and a head having a greater diameter than a shaft is provided instead of or in addition to bone threads for engagement of an adjacent upper vertebral structure.

DESCRIPTION OF THE PREFERRED EMBODIMENT

Figure 7:
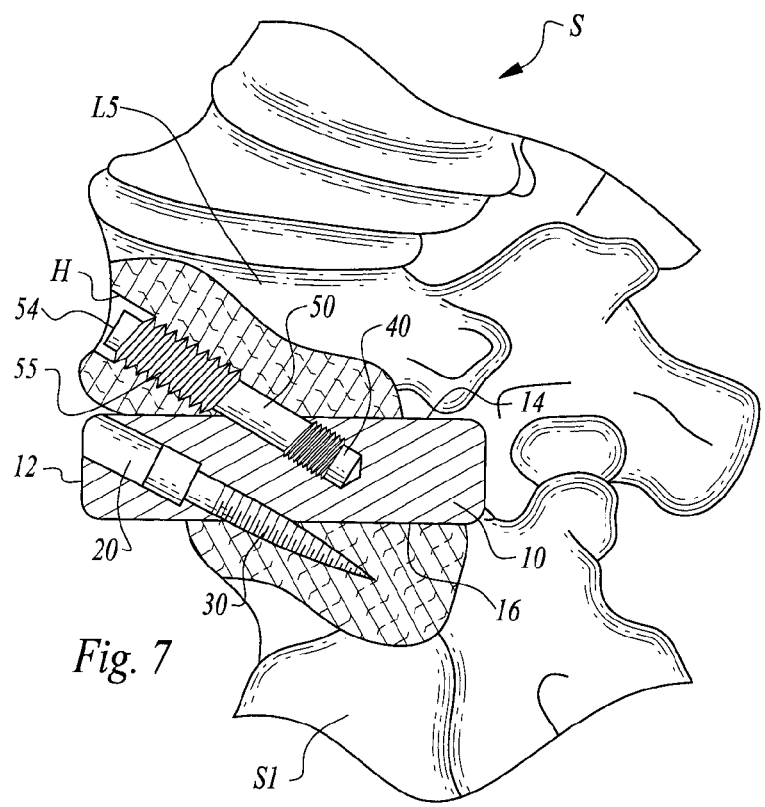
FIG. 7 is a side elevation view similar to that which is shown in FIG. 2, but with the tool removed and after completion of the interbody fusion procedure, with the interbody fusion cage fastened to both the cephalid L5 vertebra and the caudal S1 sacrum.

Referring to the drawings, wherein like reference numerals represent like parts throughout the various drawing figures, reference numeral 10 is directed to a cage implant for use in a vertebral interbody fusion procedure (FIGS. 2 and 7), according to a preferred embodiment of this invention. The implant 10 is utilized as part of a system 100 which includes a guide tool 60, drill 70 or other hole forming tool and bone screws 30 and hybrid screws 50 for securing of the implant 10 to adjacent structures such as the L5 vertebra and the S1 sacrum adjacent the implant, when used at the L5/S1 joint. Following the system 100 of this invention, the implant 10 is mechanically secured to both cephalid and caudal adjacent structures for secure fixation of the implant 10 during fusion of the adjacent vertebral structures together. While depicted primarily for interbody vertebral fusion, and especially fusion of portions of the lumbar spine S, and in particular the L5/S1 joint, the implant 10 and system 100 of this invention could be utilized for fusion of other bones or other structures together with modification of size and shape to match varying anatomy for such other uses.

Figure 2:
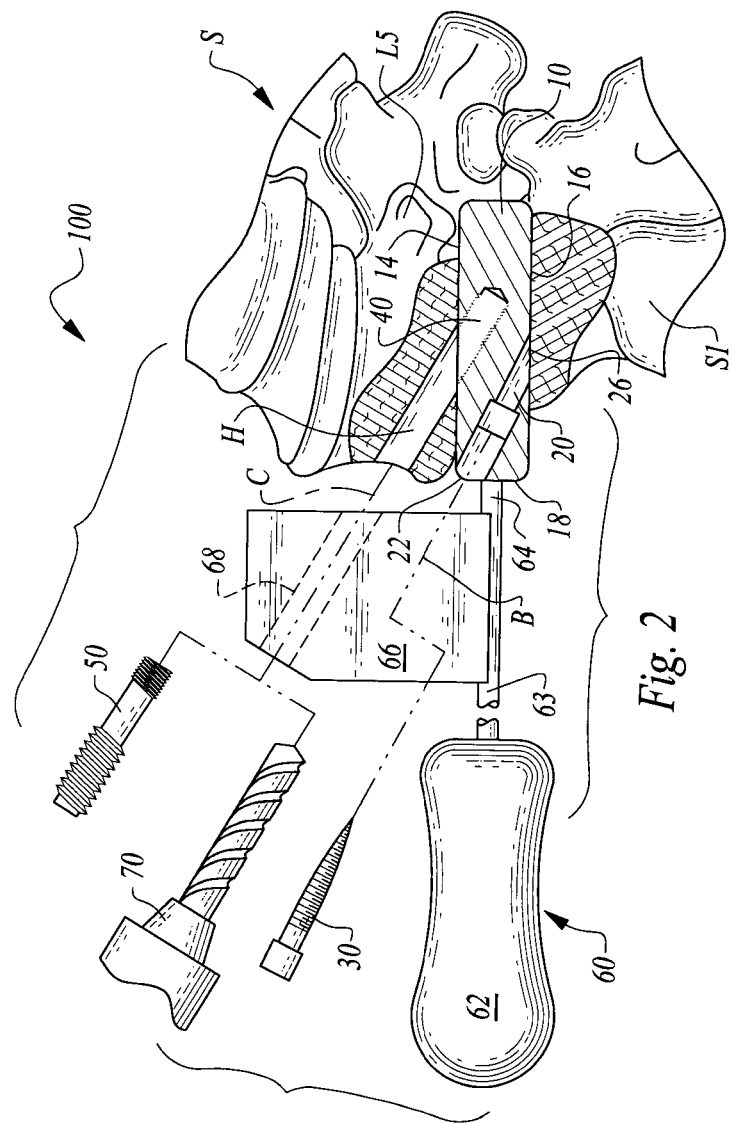
FIG. 2 is a side elevation view of a portion of that which is shown in FIG. 1 after a disk has been removed from the L5/S1 joint and the implant according to this invention has been placed therein, and with portions of vertebrae adjacent the implant cut away and with the cage implant shown in full section to reveal interior structures of the implant and operation of the guide tool and alignment of various screws for secure attachment of the cage implant to the L5 vertebra and to the S1 sacrum.
Figure 1:
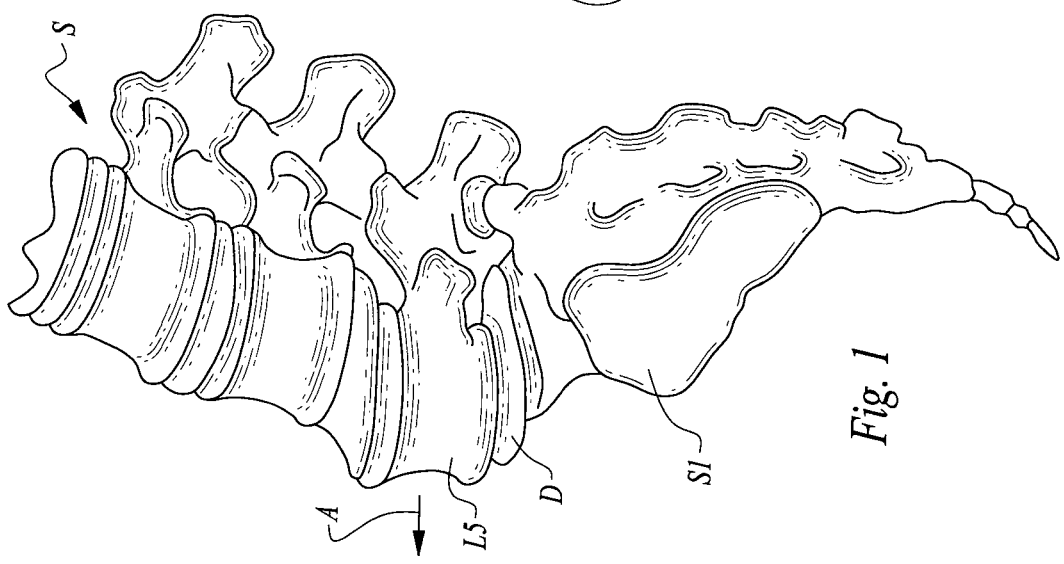
FIG. 1 is a side elevation view of the lumbar spine of a human including the sacrum and illustrating a spine exhibiting spondylolisthesis, and showing an L5/S1 joint which is a candidate for fusion utilizing the implant of this invention and according to the method of this invention.

In essence, and with particular reference to FIGS. 1 and 2, basic details of the implant 10 of this invention and other portions of the system 100 are described, according to this preferred embodiment. The implant 10 is a rigid cage structure sized to fit within an interbody space between adjacent structures to be fused together, such as adjacent vertebrae, and in this example the L5 vertebrae and the S1 sacrum. The implant 10 can have any of a variety of different geometries and configurations known for interbody fusion cages, with the implant 10 depicted herein having a generalized shape. The implant 10 includes standard bores passing entirely through the implant 10. These standard bores are oriented to allow standard bone screws to pass into the standard bores and thread into the sacrum S1 or other structure adjacent a caudal side of the implant 10. The standard bone screw 30 is thus utilized to secure the implant 10 to the sacrum S1.

Upper bores 40 are provided extending into a cephalid surface of the implant 10. A hybrid screw 50 is provided to secure the L5 vertebra or other structure adjacent a cephalid side of the implant 10 to the implant 10 through the upper bores 40. To allow this hybrid screw 50 to pass into the upper bores 40, holes H must first be formed in the L5 vertebra, or other structure adjacent the cephalid side of the implant 10, which are precisely aligned with the upper bores 40. A guide tool 60 is provided which is removably attachable to the implant 10. This guide tool 60 includes guide bores 68 which are aligned with the upper bores 40 in the implant 10. A drill 70 or other cutting tool can pass through the guide bores 68 to form the holes H aligned with the upper bores 40 in the implant 10. The hybrid screws 50 can then pass through these holes H and be threaded into the upper bores 40, so that the implant 10 can be securely attached to the L5 vertebra or other vertebra on a cephalid side of the implant 10. In this way, the implant 10 is securely attached to adjacent structures, such as the L5 vertebra and the S1 sacrum, on either side of the implant 10 for secure holding of the L5 vertebra and S1 sacrum or other adjacent vertebrae together during the fusion process.

More specifically, and with particular reference to FIGS. 2, 3, 6 and 7, details of the implant 10 are described, according to this most preferred embodiment. Interbody fusion cages such as the implant 10 come in a variety of different sizes, shapes and configurations, and exhibiting a variety of different surfaces and attributes, to optimize placement within an intervertebral space and fixation of adjacent vertebrae during a fusion procedure. The implant 10 of this invention can be utilized with a variety of such cages, so that the implant 10 generally references some form of cage or other interbody implant without particular requirement of any details of this cage implant 10.

Generally, the implant 10 includes a cephalid surface 14 opposite a caudal surface 16, which are spaced apart generally by a height of the implant 10. An anterior surface 12 is provided generally extending between the cephalid surface 14 and the caudal surface 16. This anterior surface 12 generally defines a portion of the implant 10 which is on an anterior side of the implant 10. These surfaces 12, 14, 16 could have a variety of different contours including generally flat, curving, or with other geometries or surface attributes as are known in the spinal fusion cage arts.

The implant 10 includes a tool port 18, preferably in the anterior surface 12. This tool port 18 is most preferably in the form of a threaded blind bore extending into the anterior surface 12 perpendicular to the anterior surface 12. This tool port 18 is provided for secure but removable attachment of the guide tool 60 thereto. The tool port 18 could have a configuration other than that of a threaded blind bore, with the primary function of the tool port 18 being secure removable attachment of the guide tool 60 to the implant 10 in a precise alignment between the guide tool 60 and the implant 10.

Most preferably, when the tool port 18 is in the form of a blind threaded bore, threads are formed and the bore formed so that the coupling tip 64 of the guide tool 60 which threads into this tool port 18 bottoms out within a bottom of the tool port 18 before the threads wedge the coupling tip 64 too tightly into the tool port 18. In this way, the guide tool 60 stops at a reliable rotational orientation relative to the implant 10, such that guide bores 68 associated with the guide tool 60 are reliably aligned precisely with the upper bores 40 in the implant 10. As a further alignment aid, a stop could be placed within or adjacent the tool port 18 which acts on the guide tool 60 to stop and hold its orientation where desired after coupling to the tool port.

The implant 10 preferably has both standard bores 20 and upper bores 40. In alternative embodiments, the implant 10 could be provided merely with the upper bores 40. Also, it is conceivable that only one standard bore 20 would be provided, or that more than two standard bores 20 would be provided into the implant 10. Similarly, while two upper bores 40 are provided extending along non-parallel centerlines, only one upper bore 40 could be provided or more than two upper bores 40 could be provided according to alternatives to this invention. The standard bores 20 and the upper bores 40 could be oriented parallel to each other when viewed from the side (FIGS. 2, 3 and 7) or could be otherwise oriented. Such a generally parallel orientation minimizes the area needed by a surgeon outside the surgical site to utilize the drill 70 or other cutting tool and to place the screws 30, 50 into the implant 10.

The standard bores 20 preferably pass entirely through the implant 10, extending in this preferred embodiment from the anterior surface 12 through the caudal surface 16 along bone screw axis B. Preferably, two such standard bores 20 are provided. These standard bores 20 thus have an entrance 22 adjacent the anterior surface 12 and a exit 26 adjacent the caudal surface 16. The entrance 22 can be near a junction between the anterior surface 12 and the cephalid surface 14, or conceivably slightly onto the cephalid surface 14, but near the anterior surface 12.

A step 24 is preferably provided between the entrance 22 and the exit 26 in the standard bores 20. This step 24 provides a shelf against which a bone screw head 32 of a standard bone screw 30 can abut when the standard bone screw 30 has been passed through the standard bore 20 and threaded into the S1 sacrum or other vertebrae or other structure on a caudal side of the implant 10. Preferably, the standard bone screw 30 includes the bone screw head 32 opposite a tip 36 with bone screw threads 34 adjacent the tip 36 and extending up toward the bone screw head 32. These bone screw threads 34 are cancellous threads or otherwise threads formed for engagement with bony structures such as within the S1 sacrum. These bone screw threads 34 can be configured to tap complementary threads in the sacrum S1.

As an alternative, a tapping tool can be utilized and a drill utilized to first drill a hole in the sacrum S1 and then form threads in the hole formed in the sacrum S1, so that the bone screw 30 does not need to form a hole and/or form threads in the sacrum S1, or other vertebrae or other structure, but rather merely is threaded into such a hole. As another alternative, the standard bone screw 30 could be a cannulated bone screw which is configured to follow a guide wire which has been previously fitted into the sacrum S1, such as with the assistance of a fluoroscope to ensure precise orientation of the standard bone screws 30. Most preferably, the standard bone screws 30 are oriented non-parallel to each other, for maximum mechanical coupling of the implant 10 to the sacrum S1 or other vertebrae or other structure adjacent the caudal surface 16 of the implant 10.

As shown in FIG. 2, portions of the tool 60 can conceivably block the standard bores 20 in the implant 10. The standard bone screws 30 can be placed into the standard bores 20 when the guide tool 60 is detached from the implant 10, or the guide tool 60 can be provided with holes or a shape which leaves the standard bores 20 substantially open so that the guide tool 60 can be attached to the implant 10 when the standard bone screws 30 are attached to the implant 10 and to the sacrum S1 or other vertebrae or other structure on a caudal side of the implant 10. As the standard bone screws 30 are tightened, the bone screw head 32 abuts against the step 24 and the implant 10 is drawn tight against the sacrum S1 or other vertebral structure adjacent the caudal surface 16 of the implant 10.

The upper bores 40 preferably are blind bores which extend from an entrance 42 and terminate within an interior of the implant 10. Female machine threads 44 are formed on these upper bores 40. As an alternative, the upper bores 40 could pass entirely through the implant 10 out the caudal surface 16, and with the entrance 42 still located in the cephalid surface 14. If the upper bores 40 are in the form of such throughbores, the upper bores 40 could optionally have no threads therein.

Before the upper bores 40 can be utilized, holes H are formed in the L5 vertebra or other vertebral structure adjacent the cephalid surface 14 of the implant 10. Once such a hole H has been formed, a hybrid screw 50 can be passed through this hole H and with male machine threads 57 on a distal end 56 of the hybrid screw 50 sized to match the female machine threads 44 in the upper bore 40 for securing of the hybrid screw 50 to the implant 10.

The hybrid screws 50 are configured to engage both the implant 10 and the L5 vertebra or other vertebral structure adjacent the cephalid surface 14 of the implant 10. In the preferred embodiment, the hybrid screw 50 includes a proximal end 52 opposite a distal end 56. A hybrid screw head 54 is provided at the proximal end 52. A torque applying structure is associated with the hybrid screw head 54, such as a allen wrench recess formed in the hybrid screw head 54. Such a recess is shown in broken lines in FIGS. 4 and 5.

Bone threads 55 are provided adjacent the proximal end 52 and with male machine threads 57 provided adjacent the distal end 56. The male machine threads 57 are referred to as "machine threads" because they are configured to thread into the female machine threads 44 pre-formed in the upper bores 40, with precise matching of pitch angles and major and minor diameters for secure attachment of the male machine threads 57 with the female machine threads 44 in the upper bores 40.

The bone threads 55 are configured to engage walls of the hole H formed in the L5 vertebra or other vertebral structure adjacent the cephalid surface 14 of the implant 10. In one embodiment, the hole H has a diameter similar to a minor diameter of the hybrid screw 50. The bone threads 55 thus thread into walls of the hole H as the hybrid screw 50 is advanced along a centerline of the hole H and the upper bores 40. As the hybrid screw 50 advances, the male machine threads 57 adjacent the distal end 56 engage the female machine threads 44 and the hybrid screw 50 is then coupled through both the male machine threads 57 engaging the female machine threads 44 in the upper bores 40 of the implant 10, as well as the bone threads 55 simultaneously engaging walls of the hole H in the L5 vertebra or other vertebral structure adjacent the cephalid surface 14 of the implant 10. The bone threads 55 can be self-tapping, such as by including a self-tapping cutting groove 160 in the alternative hybrid screw 150 depicted in FIG. 5.

Figure 5:
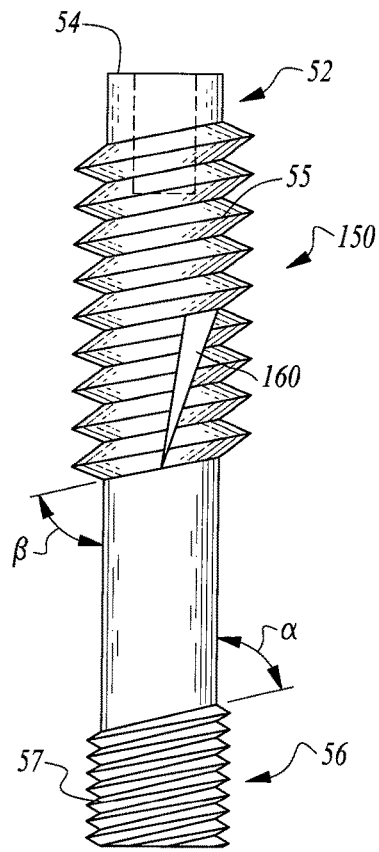
FIG. 5 is a side elevation view similar to that which is shown in FIG. 4, but for an embodiment of the screw which includes a self-tapping cutting groove therein, and illustrating pitch angles for the various threads.

Also in FIG. 5, pitch angles for the male machine threads 57 and the bone threads 55 are depicted. Angle $\alpha$ depicts a pitch angle for the male machine threads 57. Angle $\beta$ depicts the pitch angle for the bone threads 55. Preferably, the pitch angle for the male machine threads 57 and the pitch angle for the bone threads 55 are substantially identical. Because the male machine threads 57 in this embodiment are finer than the bone threads 55, the male machine threads 57 can be compound threads to allow the pitch angles $\alpha$, $\beta$ to match each other. As another alternative, the male machine threads 57 could be provided no finer than the bone threads 55.

In one embodiment, a slight differential is provided between the pitch angle $\alpha$ and the pitch angle $\beta$, with the pitch angle $\alpha$ being slightly steeper than the pitch angle $\beta$. In this way, portions of the hybrid screw 50 adjacent the distal end 56 advance at a greater rate per turn of the hybrid screw 50 than portions of the screw 50 adjacent the proximal end 52, so that the implant 10 is drawn toward the L5 vertebra or other vertebral structure adjacent the cephalid surface 14 of the implant 10. With such a configuration, an initially somewhat loose threading of the hybrid screw 50 through the hole H and into the upper bore 40 becomes a tight fit as the hybrid screw 50 continues to be rotationally advanced into the upper bores 40 and this differential in the pitch angles of the male machine threads 57 and bone threads 55 cause a tightening of the L5 vertebra or other vertebral structure adjacent the cephalid surface 14 of the implant 10 to be drawn tightly against the cephalid surface 14 of the implant 10.

Figure 4:
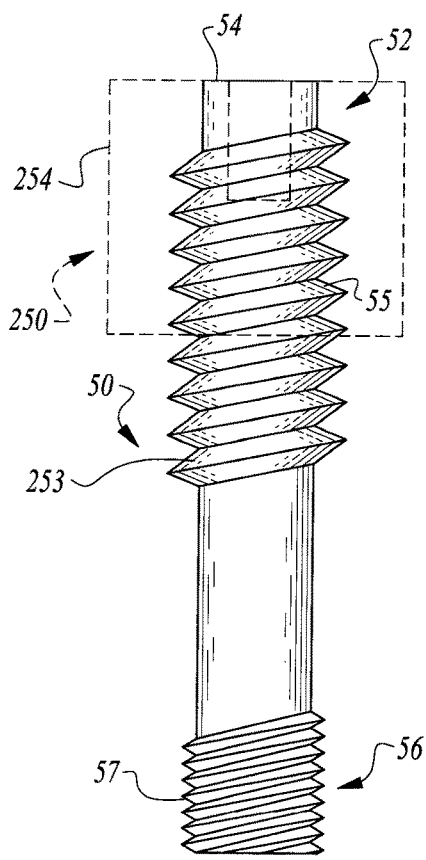
FIG. 4 is a side elevation view of a hybrid screw for use according to this invention to secure the L5 vertebra (or other structure adjacent a cephalid side of the implant) to the implant.

In another alternative depicted in FIG. 4 in broken lines, a further alternative hybrid screw 250 is depicted which has no bone threads thereon. Rather, an alternative hybrid screw head 254 is provided which has a diameter greater than that of an alternative hybrid screw shaft 253. In this embodiment, the hole H would be provided with a step therein, such as midway between an anterior side of the L5 vertebra and a surface of the L5 vertebra adjacent the cephalid surface 14 of the implant 10. The alternative hybrid screw head 254 would abut this shelf and then apply a compressing force on the L5 vertebra compressing it against the implant 10 as further turning of the hybrid screw 50 and further engagement of the male machine threads 57 of the hybrid screw 50 with the female machine threads 44 in the upper bores 40 of the implant 10 draws the hybrid screw 50 further down into the implant 10.

To form such a stepped hole in the L5 vertebra, or other vertebral structure adjacent the cephalid surface 14 of the implant 10, a drill bit can be utilized which has a stepped character. As another alternative, two separate drill bits having different sizes can be sequentially utilized. A first smaller drill bit would follow a centerline C entirely through the L5 vertebra to form the hole H. Then a second larger drill bit would be advanced only partway along the same centerline C, with perhaps a stop on the drill bit or other technique to precisely control a depth of the larger diameter portion of the hole H.

Hybrid screws 50 having such an alternative hybrid screw head 254 and without bone threads (or optionally with both the alternative hybrid screw head 254 and bone threads 55) could be provided with different lengths in small increments, so that if the hybrid screw 50 is found to be too long or too short, a separate hybrid screw can be selected which has an appropriate length to maximize secure attachment of the L5 vertebra (or other vertebral structure adjacent the cephalid surface 14 of the implant 10) to the upper bores 40 of the implant 10.

Figure 3:
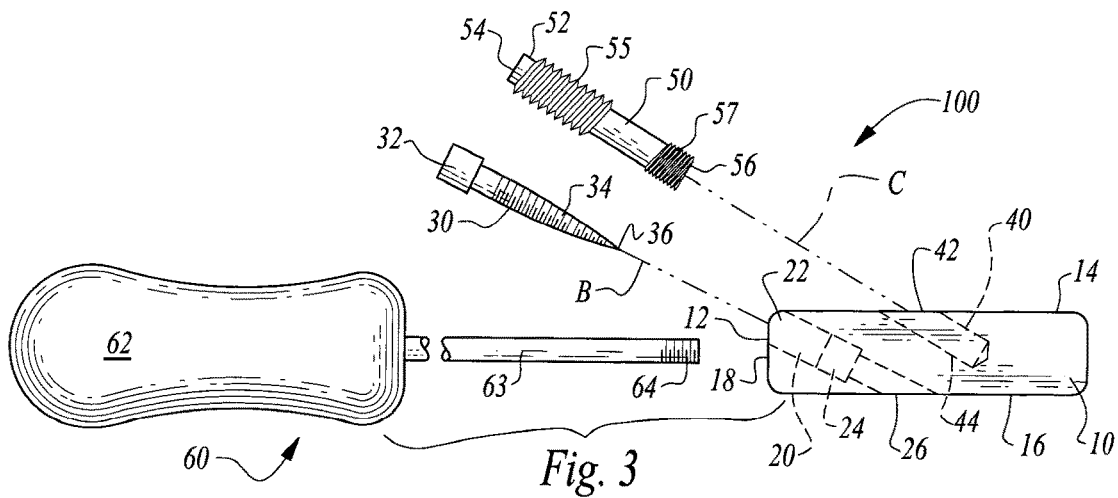
FIG. 3 is a side elevation exploded view of the implant, tool and screws of FIG. 2, but shown without the spine portions present, and without the guide block and associated guide bores, and with interior structures of the implant shown in broken lines.
Figure 6:
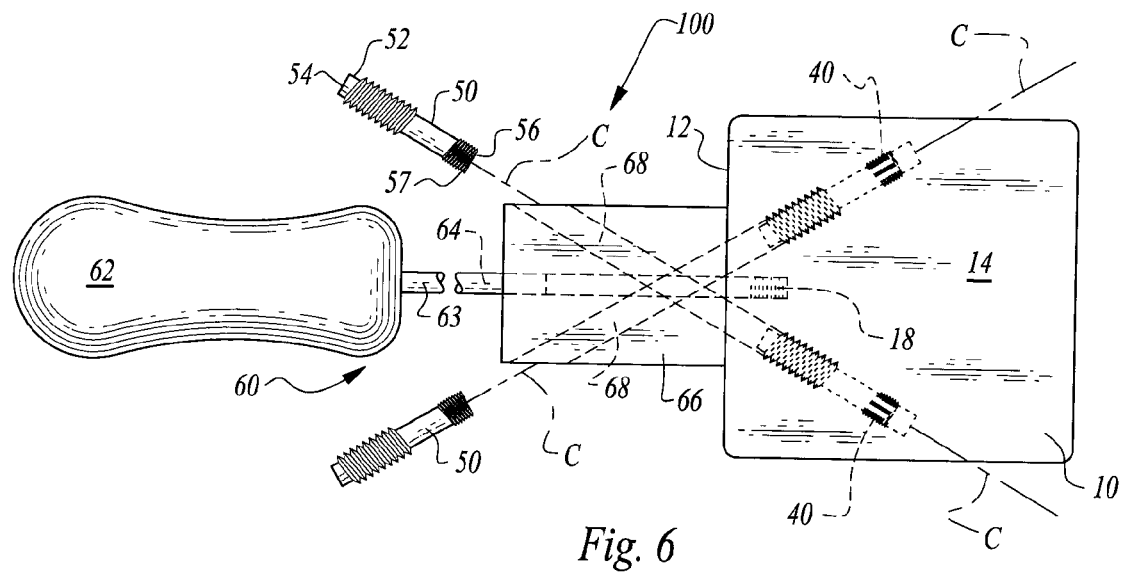
FIG. 6 is a top plan view of the implant and tool and attachment threads with broken lines depicting paths of the guide bores in the guide tool and a tool port within the implant for removable attachment of a coupling tip of the guide tool thereto.

With particular reference to FIGS. 2, 3 and 6, details of the guide tool 60, according to one embodiment of the system 100 of this invention, are described. In operating the system 100 and method of this invention it is important that the hole H be precisely formed that is aligned with the centerline C of the upper bores 40 in the implant 10. To achieve this precise alignment, the guide tool 60 is provided. The guide tool 60 is removably attachable securely to the implant 10 so that guide bores 68 in the guide tool 60 can be precisely aligned with the upper bores 40 in the implant 10 along the common centerline C.

In the preferred embodiment, this guide tool 60 includes a handle 62 coupled to one end of a guide tool shaft 63 with a coupling tip 64 at an opposite end of the guide tool shaft 63. This coupling tip 64 is threaded to thread into the tool port 18 in the anterior surface 12 of the implant 10. As an alternative, some other form of rigid removable coupling can exist between the guide tool 60 and the implant 10 for secure attachment of the guide tool 60 to the implant 10. Importantly, this attachment not only provides for elimination of movement between the implant 10 and the guide tool 60, but also provides for precise orientation of guide bores 68 of the guide tool 60 relative to the implant 10.

The guide tool shaft 63 in this embodiment supports a guide block 66 extending therefrom. Multiple guide bores 68 pass through this guide block 66 which guide bores 68 are aligned with the upper bores 40 in the implant 10 when the coupling tip 64 of the guide tool 60 is coupled to the implant 10. Once so attached, the drill 70 can be utilized passing through the guide bores 68 to form the holes H through which the hybrid screws 50 pass, for secure attachment to the upper bores 40 of the implant 10.

While the guide tool 60 is described in this manner, a variety of different guides could be provided, so long as guide bores are oriented where required and precisely aligned with the centerline C of the upper bores 40 of the implant 10, so that a drill 70 or other cutting tool can be precisely passed along this centerline C to cut a hole through the L5 vertebra or other vertebral structure adjacent the cephalid surface 14 of the implant 10, to form the hole H precisely aligned with the upper bores 40 in the implant 10. In one embodiment, the guide tool 60 is attached to multiple locations on the anterior surface 12 or other portions of the implant 10, to ensure very precise alignment of the guide bores 68 associated with the guide tool 60 with the centerlines C of the upper bores 40 in the implant 10.

This disclosure is provided to reveal a preferred embodiment of the invention and a best mode for practicing the invention. Having thus described the invention in this way, it should be apparent that various different modifications can be made to the preferred embodiment without departing from the scope and spirit of this invention disclosure. When structures are identified as a means to perform a function, the identification is intended to include all structures which can perform the function specified. When structures of this invention are identified as being coupled together, such language should be interpreted broadly to include the structures being coupled directly together or coupled together through intervening structures. Such coupling could be permanent or temporary and either in a rigid fashion or in a fashion which allows pivoting, sliding or other relative motion while still providing some form of attachment, unless specifically restricted.

What is claimed is:

1. A combination interbody implant and vertebral screw guide, comprising in combination:
    an implant having an anterior surface and a cephalid surface opposite a caudal surface;
    said implant having at least one bore extending into said cephalid surface thereof, along a bore centerline extending from said cephalid surface toward said caudal surface and away from said anterior surface;
    a guide removably attachable to said implant;
    said guide having a guide bore extending along a portion of said bore centerline outside of said implant; and
    wherein the combination further includes a hybrid screw with a proximal end opposite a distal end, said proximal end having a head with a torque applying interface thereon and said distal end having male threads thereon, said at least one bore in said cephalid surface of said implant having female threads therein, said male threads engaging said female threads, said hybrid screw having a bone engagement structure on a proximal side of said male threads and spaced from said male threads for engagement of a vertebra adjacent said cephalid surface of said implant.

2. The combination of claim 1 wherein said at least one bore in said implant is a blind bore extending into said cephalid surface of said implant, said blind bore including female threads on an interior surface thereof.

3. The combination of claim 1 wherein said at least one bore in said implant is a throughbore extending through both said cephalid surface and said caudal surface, the combination including a screw having a length greater than a length of said throughbore, such that said screw is adapted to have portions thereof extending from both said cephalid surface and said caudal surface for engagement of structures on both a cephalid side of said implant and a caudal side of said implant.

4. The combination of claim 1 wherein said guide attaches to said implant through said anterior surface of said implant, with said guide bore of said guide located substantially on an anterior and cephalid side of said implant, said guide bore having a width at least as great as a width of said at least one bore extending into said cephalid surface of said implant.

5. The combination of claim 4 wherein a threaded tool port is located in said anterior surface of said implant, said guide including a threaded coupling tip thereon sized to thread into said threaded tool port in said anterior surface to removably attach said guide to said implant.

6. The combination of claim 5 wherein said guide includes an elongate guide tool shaft with said threaded coupling tip at an end of said elongate guide tool shaft, said elongate guide tool shaft having a handle on an end thereof opposite said threaded coupling tip, and a guide block having said guide bore therein at least temporarily fixed to said elongate guide tool shaft between said handle and said threaded coupling tip.

7. The combination of claim 1 wherein at least one additional bore extends through said implant along a line extending from said anterior surface through said caudal surface, and at least one bone screw is sized to pass through said at least one additional bore and thread into a structure adjacent said caudal surface of said implant.

8. An implant for fusion of adjacent structures together, the implant comprising in combination:
    an anterior surface and a cephalid surface opposite a caudal surface;

at least one bore extending into said cephalid surface, along a bore centerline extending from said cephalid surface toward said caudal surface and away from said anterior surface; and wherein the combination further includes a hybrid screw with a proximal end opposite a distal end, said proximal end having a head with a torque applying interface thereon and said distal end having male threads thereon, the hybrid screw male threads engaging female threads in said at least one bore extending into said cephalid surface of said implant, said hybrid screw having a bone engagement structure on a proximal side of said male threads and spaced from said male threads for engagement of a vertebra adjacent said cephalid surface of said implant.

9. The implant of claim 8 wherein said bone engagement structure of said hybrid screw includes bone threads thereon, with said male threads closer to the distal end of the hybrid screw than said bone threads.

10. The implant of claim 9 wherein said bone threads and said male threads have a differing pitch angle to cause a structure adjacent said cephalid surface of said implant to be drawn toward said implant as said hybrid screw is threaded into said at least one bore extending into said cephalid surface of said implant.

* * * * *